United States Patent [19]

Matsuda et al.

[11] Patent Number: 5,348,873
[45] Date of Patent: Sep. 20, 1994

[54] IMMOBILIZATION OF AN ANTI-THROMBOGENIC SUBSTANCE WITH A PHOTO-REACTIVE AZIDE AND A PHOTO-CROSSLINKING MATERIAL

[75] Inventors: Takehisa Matsuda; Yasuhide Nakayama, both of Minou; Takashi Sugawara, Ikeda, all of Japan

[73] Assignee: K.K. Vayu, Japan

[21] Appl. No.: 963,089

[22] Filed: Oct. 19, 1992

[30] Foreign Application Priority Data

Nov. 1, 1991 [JP] Japan .................. 3-288062

[51] Int. Cl.$^5$ .................. C12N 11/04; C12N 11/06; C12N 11/08; A61F 13/00
[52] U.S. Cl. .................. 435/182; 424/422; 424/423; 435/180; 435/181; 514/822
[58] Field of Search .................. 435/180, 181, 182; 530/815, 817; 424/422, 423; 514/822

[56] References Cited

U.S. PATENT DOCUMENTS

| | | | |
|---|---|---|---|
| 5,061,750 | 10/1991 | Feijen et al. | 435/180 X |
| 5,071,909 | 12/1991 | Pappin et al. | 435/182 X |
| 5,134,057 | 7/1992 | Kuypers et al. | 430/325 |

*Primary Examiner*—David M. Naff
*Attorney, Agent, or Firm*—Davis, Bujold & Streck

[57] ABSTRACT

An anti-thrombogenic substance is immobilized on a base of a medical device to impart anti-thrombogenic properties to the medical device. The method comprises the steps of applying a photo-reactive azide derivative macromolecular material to a base to form a bonding layer, coating the bonding layer with a macromolecular layer composed of a water-soluble photo-crosslinking macromolecular material containing the anti-thrombogenic substance, and irradiating the base with ultraviolet light with the bonding layer and the macromolecular layer formed thereon to develop inter-molecular covalent bonding in the bonding layer. The macromolecular layer containing the anti-thrombogenic substance is thus fixed onto the base. Concurrently, the anti-thrombogenic substance is immobilized in the macromolecular layer which is crosslinked. The azide derivative can be poly-m-azidostyrene, copolymers, of poly-m-aziodstyrene with styrene and copolymers of poly-m-azidostyrene with methyl methacrylate. The water-soluble photo-crosslinking macromolecular material can be a copolymer of a photo-dimeric monomer with a water-soluble monomer or a copolymer of a photo-reactive azide with a water-soluble monomer.

19 Claims, 6 Drawing Sheets

IMMOBILIZATION OF AN ANTI-THROMBOGENIC SUBSTANCE WITH A PHOTO-REACTIVE AZIDE AND A PHOTO-CROSSLINKING MATERIAL

BACKGROUND OF THE INVENTION

This invention relates to a method for immobilizing an anti-thrombogenic substance inside a macromolecular material bonded onto a base by photopolymerization, which is used as a base material of a medical device to be placed in contact with blood or to be inserted into a human or other animal body for use.

Various materials for imparting anti-thrombogenic or anticoagulant properties to the medical device have been researched and developed. Synthetic material having complete anti-thrombogenic or anticoagulant properties, however, has not been developed yet.

One approach for obtaining the anticoagulant properties has been studied. By this approach, an anticoagulant material is formed of heparin. Heparin devitalizes the blood coagulant system in vivo and biologically actively prevents the aggregation of platelets. Research and development has revealed the following major conventional methods for immobilizing heparin.

(1) A simple physical blending method. In this method, an aqueous solution of heparin and a solution of thermosetting resin are blended, applied to a surface of a base, and heated, thereby forming a membrane of thermosetting resin on the base. The membrane polymer is crosslinked by chemical reaction resulting from heating and is thereby caused to contain the heparin.

(2) An ionic bonding method. In this method, a blend or copolymer of a cationic substance in a polymer is immersed in a highly concentrated aqueous solution of heparin. By ionic bonding, heparin is immobilized in the blend or the copolymer.

(3) A covalent bonding method. In this method, a functional group or a bonding group R is introduced into heparin by applying a chemical modification of heparin. Heparin is immobilized on the surface of a base by a chemical reaction. Alternatively, by chemically modifying the surface of a base, the bonding group R is introduced. Such chemical modification causes heparin to be immobilized on the surface of the base.

The aforementioned methods, however, have the following problems, respectively.

In the physical blending method, the heparin is dispersed non-uniformly in a solvent. As a result, the prepared film is not uniform. Furthermore, since the thermosetting resin membrane is bonded onto the base with insufficient bonding force, the membrane gradually peels off from the base when the film is used in blood. Also, in the same way as in the ionic bonding method, heparin is easily discharged from the membrane. Therefore, the effect of the anti-thrombogenic properties of heparin can be expected for only a short time period.

In the covalent bonding method, the insolubility of heparin in the organic solvent restricts the chemical reaction. Moreover, since only a small quantity of heparin is bonded to the base, the anticoagulant properties are developed only for a very short time period.

SUMMARY OF THE INVENTION

Wherefore, an object of this invention is to provide a device and a method for immobilizing an anti-thrombogenic substance on a base of the device to impart superior anti-thrombogenic properties to that device.

To attain this or other object, the present invention provides a method for immobilizing an anti-thrombogenic substance comprising the steps of:

coating a surface of a base with a bonding layer comprising a photo-reactive azide derivative macromolecular material which provides covalent bonding when exposed to light;

applying an aqueous solution onto the bonding layer coated base to coat the bonding layer with a macromolecular layer, the aqueous solution including a water-soluble photo-crosslinking macromolecular material and the anti-thrombogenic substance;

irradiating the base with the bonding layer and the macromolecular layer formed thereon with light to chemically fix the macromolecular layer on the base via the bonding layer, the water-soluble photo-crosslinking macromolecular material becoming insoluble and maintaining a gel condition thereof after being crosslinked by said irradiation; wherein the anti-thrombogenic substance is retained in the macromolecular layer.

BRIEF DESCRIPTION OF THE DRAWINGS

The invention will now be described, by way of example, with reference to the accompanying drawings, in which.

DETAILED DESCRIPTION OF THE PREFERRED EMBODIMENTS

Figure 1:
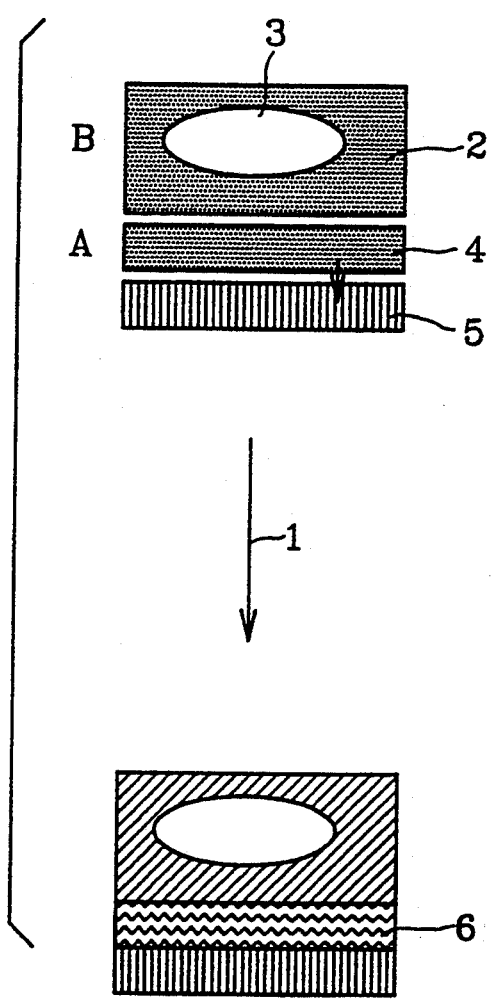
FIG. 1 is an explanatory view illustrating a method of immobilizing an anti-thrombogenic substance according to a first embodiment of the present invention.

In the method of a first embodiment for immobilizing the anti-thrombogenic substance shown in FIG. 1, when layers A and B are irradiated with ultraviolet light 1, the layer B being a water-soluble photo-crosslinking macromolecular material 2 containing an anti-thrombogenic substance 3 and the layer A being a photo-reactive azide derivative macromolecular material 4 formed on a base 5, an intermolecular covalent bonding is established in the layer A. The layer A then functions as a binder 6 between the layer B and the surface of the base 5. The layer B containing the anti-thrombogenic substance 3 is thus chemically fixed on the base 5. The anti-thrombogenic substance 3 contained in the layer B is immobilized in a macromolecular gel resulting from the photo-crosslinking reaction. During use in contact with blood, the immobilized anti-thrombogenic substance 3 is gradually discharged from the macromolecular gel over a long period, thereby preventing prothrombin or other blood clots from forming.

In a second embodiment, the method for immobilizing the anti-thrombogenic substance according to the invention can further have the step of physically coating the macromolecular layer containing the anti-thrombogenic substance with a hydrophilic protective layer of a water-soluble photo-crosslinking macromolecular material. By irradiating light onto the base with the bonding layer, the macromolecular layer and the hydrophilic protective layer physically formed thereon, the macromolecular layer and the hydrophilic protective layer are chemically fixed onto the base via the bonding layer, and the anti-thrombogenic substance is immobilized in the macromolecular layer. The hydrophilic protective layer decelerates the discharge of the anti-thrombogenic substance, whereby the anti-thrombogenic properties can be developed for an extended time period. The hydrophilic protective layer can be formed of a blend of a water-soluble photo-crosslinking macromolecular material and a cationic macromolecular material.

The water-soluble photo-crosslinking macromolecular material can be a water-soluble macromolecular material including a photo-reactive group showing a photo-dimeric reaction, or a water-soluble macromolecular material having a photo-reactive azide group. For example, available is a copolymer of a photo-dimeric monomer or a monomer having a photo-reactive azide group, with a water-soluble monomer such as acrylamide or dimethylacrylamide. As the photo-dimeric monomer, cinnamic acid derivative, chalcone derivative, cumarin derivative, thymine derivative or other may be used.

As the anti-thrombogenic substance, heparin, urokinase or other anti-thrombogenic or anticoagulant agent is used. Alternatively, prostacyclin or other anti-platelet aggregation agent is used.

As the photo-reactive azide derivative macromolecular material, the monomer with m-azidostyrene macromolecules or other azide group introduced therein is used. Alternatively, a copolymer of this monomer with a radical polymeric vinyl monomer such as styrene or methyl methacrylate is used.

As the base, polyethylene terephthalate or other macromolecular material can be used.

In the method for immobilizing the anti-thrombogenic substance, when the material of the bonding layer is applied onto the base, the dissolution of the material in chloroform or other organic solvent is preferable.

The material of the macromolecular layer applied to the base is preferably dried at room temperature.

When the base with at least the macromolecular layer and the bonding layer formed thereon is irradiated with light, the light source is preferably a xenon lamp or a high pressure mercury lamp with a glass filter attached thereto. For example, ultraviolet light having a wave length of about 290 nm is emitted from the light source for about 5 to about 10 minutes.

EXAMPLE ONE

A chloroform solution of poly-m-azidostyrene was applied onto a surface of a base of polyethylene terephthalate and was left to stand and dry for five minutes.

Subsequently, onto the dried surface of the prepared film was applied 100$\mu$ 1 of aqueous solution with 24 mg of the copolymer of $\beta$-cinnamoyloxy ethyl methacrylate and dimethylacrylamide and 12mg of heparin sodium salt (159 I.U./mg) dissolved therein. In the copolymer, 3.5 mol% of $\beta$-cinnamoyloxy ethyl methacrylate is introduced.

In this way, the water-soluble photo-crosslinking macromolecules containing heparin were applied to the film. Subsequent formation of a hydrophilic protective layer differs from other examples.

After the film was left to stand overnight, onto the film was further applied 50$\mu$ 1 dimethyl formamide solution with 24 mg of the copolymer of $\beta$-cinnamoyloxy ethyl methacrylate and dimethylacrylamide dissolved therein. In the copolymer, 25.0 mol% of $\beta$-cinnamoyloxy ethyl methacrylate was introduced.

After the film was left to stand further overnight, the film was irradiated by light from a 500W xenon lamp, with a glass filter of UV-29 attached thereto, for 10 minutes. Thus, heparin in the film was immobilized on the surface of the base of polyethylene terephthalate.

Figure 2:
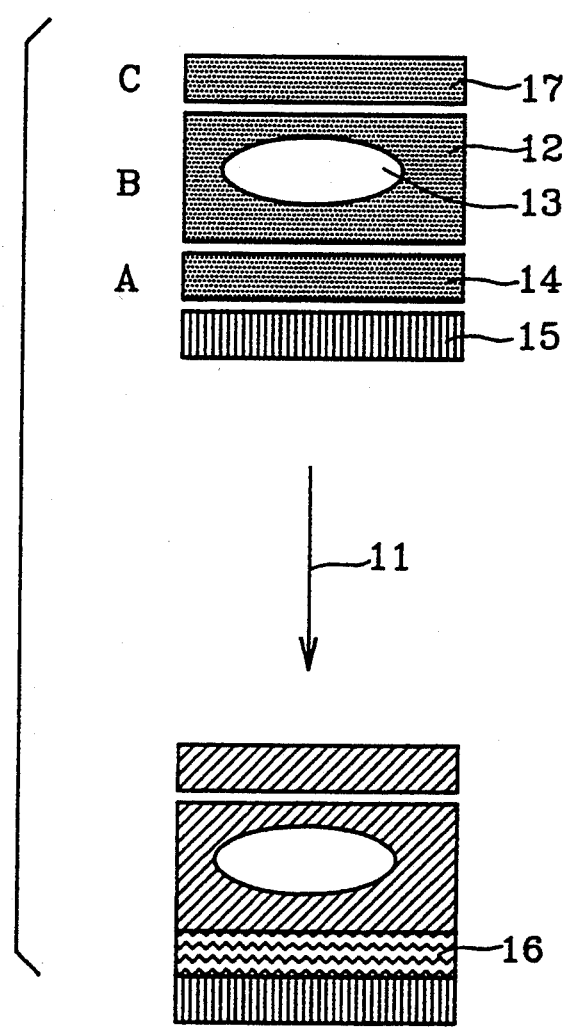
FIG. 2 is an explanatory view showing a method of immobilizing an anti-thrombogenic substance according to a second embodiment of the present invention.

In the second embodiment, as shown in FIG. 2, layer A is composed of photo-reactive azide derivative macromolecules 14, layer B is composed of water-soluble photo-crosslinking macromolecules 12 containing heparin 13, and layer C is composed of water-soluble photo-crosslinking macromolecules 17.

Specifically, in the second embodiment, the layer A is composed of poly-m-azidostyrene, the layer B is composed of the copolymer of $\beta$-cinnamoyloxy ethyl methacrylate and dimethylacrylamide, containing heparin, and the hydrophilic protective layer C is composed of the copolymer of $\beta$-cinnamoyloxy ethyl methacrylate and dimethylacrylamide.

When the layers A, B and C formed on a base 15 are irradiated with ultraviolet light 11, the layer A functions as a binder 16 and the layer B containing heparin is chemically fixed onto the base 15. At the same time, the hydrophilic protective layer C is chemically formed on the layer B.

EXAMPLE TWO

By following the procedure of the first example, water-soluble photo-crosslinking macromolecules containing heparin were applied to a base and dried. The prepared film was left to stand and dry overnight.

Subsequently, different from the first example, 50$\mu$ 1 of dimethyl formamide solution with 24 mg of poly-$\beta$-cinnamoyloxy ethyl methacrylate dissolved therein was applied to the film.

After the film was again left to stand and dry overnight in the shade, the film was irradiated with light from a 500W xenon lamp, with a glass filter of UV-29 attached thereto, for 10 minutes. By this process heparin was immobilized on the surface of the base of polyethylene terephthalate.

REFERENCE EXAMPLE

After a film was prepared and dried under the same condition as that of the first example, no ultraviolet light was radiated onto the film.

FIRST MEASUREMENT

The films resulting from the first and second examples and the reference example were respectively immersed in 500 ml of 0.2% NaCl aqueous solution while being stirred at room temperature. The quantity of heparin discharged from the surface of each film was measured against time. For the measurement, the quantity of heparin flowing into a 0.2% NaCl aqueous solution was measured by using toluidine blue coloration.

Figure 3:
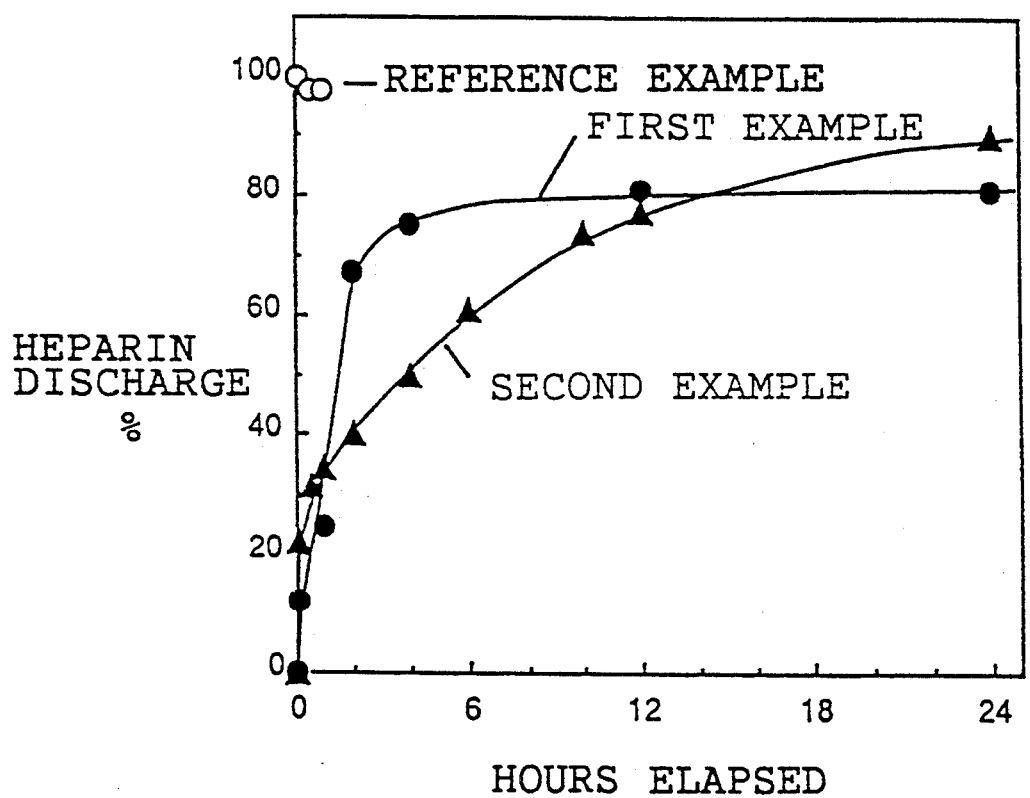
FIG. 3 is a graph showing the results of given examples of the second embodiment.

As is apparent from the graph of FIG. 3, the heparin discharge was observed for 12 hours from the film of the first example. This film has the hydrophilic protective layer composed of the copolymer of β-cinnamoyloxy ethyl methacrylate and dimethylacrylamide, with the introduction of 25.0 mol% of β-cinnamoyloxy ethyl methacrylate therein.

The heparin discharge was observed for 24 hours from the film of the second example. The film has the hydrophilic protective layer composed of poly-β-cinnamoyloxy ethyl methacrylate.

On the other hand, almost all of the heparin was discharged in five minutes from the film of the reference example.

This result makes it evident that heparin is effectively immobilized in the film by ultraviolet irradiation. The comparison between the first and second examples indicates that the increase of the percentage of cinnamoyloxy ethyl methacrylate in the hydrophilic protective layer inhibits heparin from being discharged.

EXAMPLE THREE

By following the procedure of the first example, water-soluble photo-crosslinking macromolecules containing heparin were applied and dried. Thus prepared film was left to stand and dry overnight.

Subsequently, different from the first example, 200μ 1 dimethyl formamide solution with 96 mg of the copolymer of β-cinnamoyloxy ethyl methacrylate and dimethylacrylamide dissolved therein was applied to the film. 25.0 mol% of β-cinnamoyloxy ethyl methacrylate was introduced into the copolymer.

After the film was left to stand and dry further overnight, the film was irradiated with light from a 500W xenon lamp, with a glass filter of UV-29 attached thereto, for 10 minutes. By this the heparin was immobilized on the surface of the base of polyethylene terephthalate.

The third example has more application quantity of the hydrophilic protective layer than the first example.

SECOND MEASUREMENT

The quantity of heparin discharged from the film resulting from the third example was observed against time under the same conditions as those of the first measurement.

Figure 4:
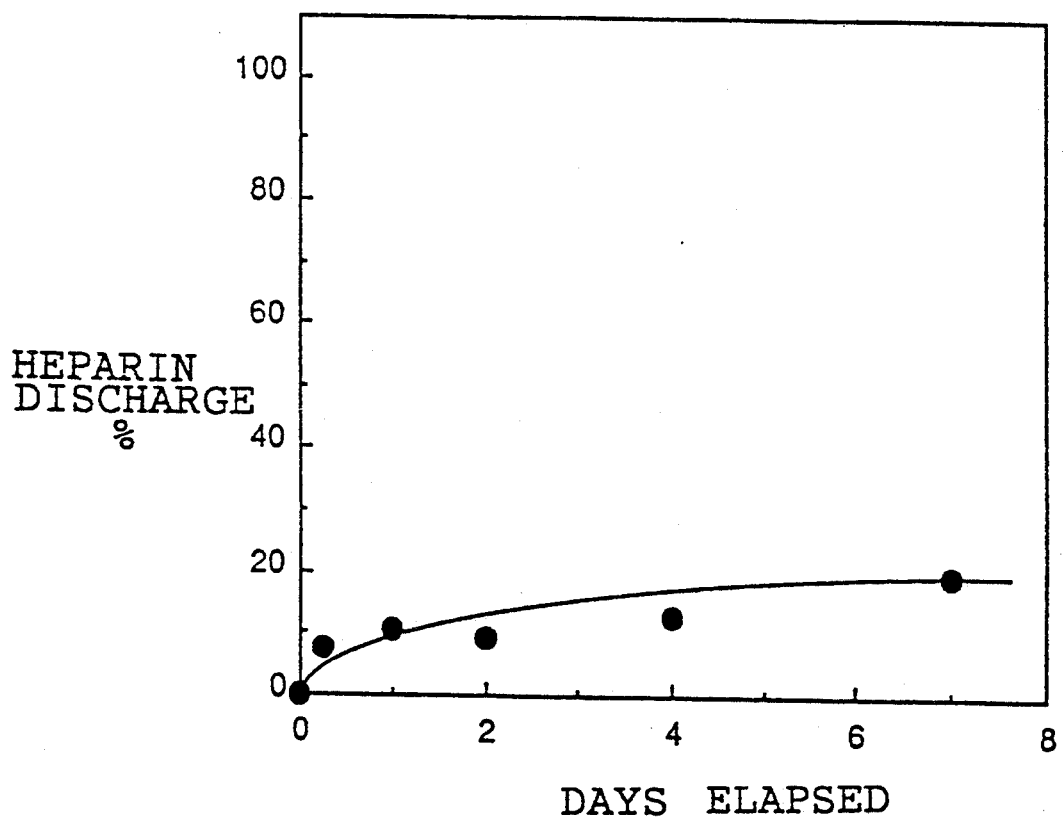
FIG. 4 is a graph showing the extended results achieved in further example of the second embodiment.

As can be seen from the graph of FIG. 4, the discharge of heparin was effectively inhibited. Even seven days after the start of the measurement, 80% or more of heparin was still immobilized in the film of the third example. A stable slow discharge of heparin was observed.

This shows that the adjustment of the application of the protective layer material can decelerate heparin discharge.

EXAMPLE FOUR

By following the procedure of the first example, the water-soluble photo-crosslinking macromolecules containing heparin were applied and dried. The prepared film was left to stand and dry overnight.

Subsequently, different from the first example, to the film was further applied 50μ 1 dimethyl formamide solution with 12 mg of the copolymer of β-cinnamoyloxy ethyl methacrylate and dimethylacrylamide dissolved therein, as well as 12 mg of a fourth class compound composed of polydimethylaminoethyl methacrylate and methyl iodide dissolved therein. 25.0 mol% of β-cinnamoyloxy ethyl methacrylate is introduced in the copolymer.

After the film was again left to stand and dry overnight in the shade, the film was irradiated with light from a 500W xenon lamp, with a glass filter of UV-29 attached thereto, for 10 minutes. By this, heparin was immobilized on the surface of the base of polyethylene terephthalate.

Figure 5:
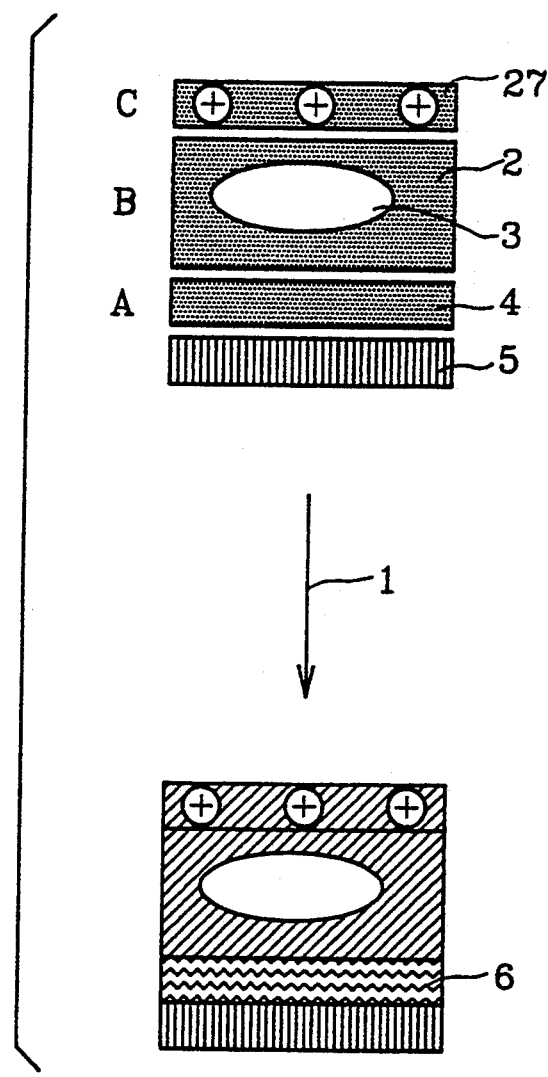
FIG. 5 is an explanatory view showing a method of immobilizing an anti-thrombogenic substance in a third embodiment of the present invention.

This is an example of a third embodiment. In the third embodiment, as shown in FIG. 5, the compositions of the layers A and B are the same as those of the second embodiment shown in FIG. 2. The hydrophilic protective layer C is, different from the second embodiment, in being a blend 27 of the copolymer of β-cinnamoyloxy ethyl methacrylate and dimethylacrylamide with the fourth class compound composed of poly-dimethylaminoethyl methacrylate and methyl iodide.

THIRD MEASUREMENT

The quantity of heparin discharged from the film resulting from the fourth example was observed against time under the same condition as that of the first measurement.

Figure 6:
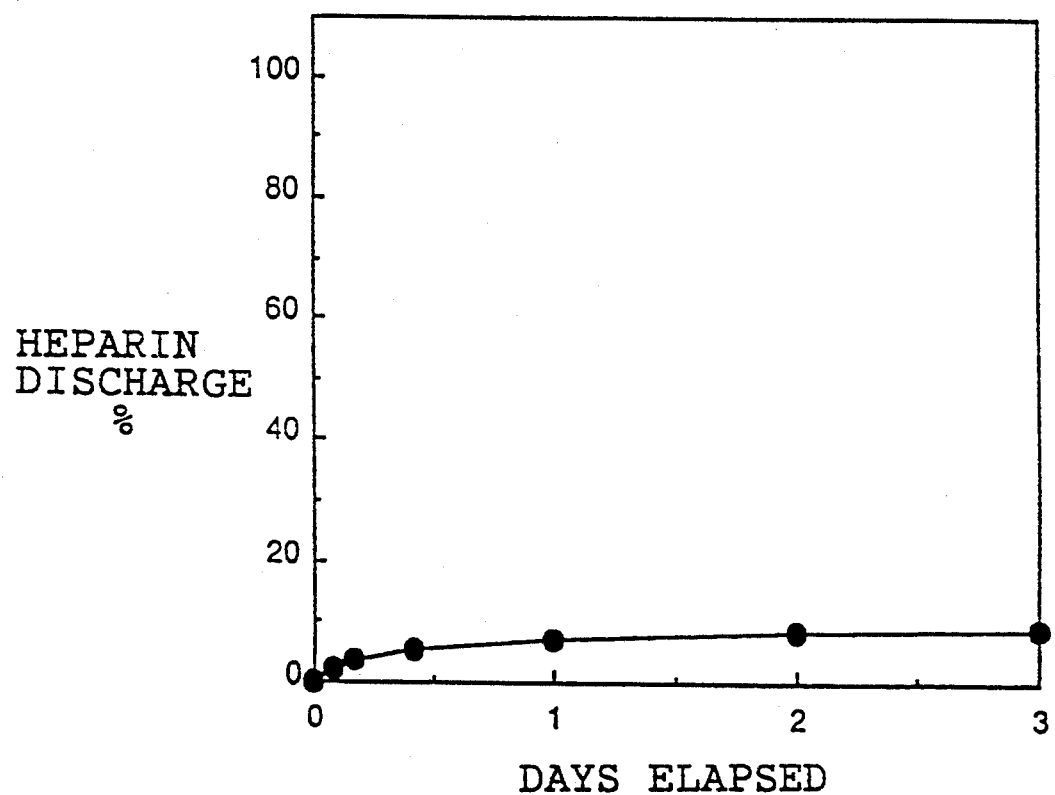
FIG. 6 is a graph showing the results of example of the third embodiment.

The graph of FIG. 6 indicates that the discharge of heparin was effectively inhibited. Even three days after the start of the measurement, 90% or more of heparin was still immobilized in the film of the fourth example. The stable gradual discharge of heparin is because heparin is adsorbed by the cationic macromolecules included in the hydrophilic protective layer C when heparin is discharged.

As a result, the blend of the cationic macromolecules in the water-soluble photo-crosslinking macromolecules in the layer C can control the speed of heparin discharge.

The method for immobilizing the anti-thrombogenic substance in the embodiments according to the present invention have the following or other advantages.

Since heparin can be immobilized onto any kind of the surface of a device base, the general-purpose properties can be enhanced.

The adjustability of the application of heparin from the water-soluble macromolecular solution makes it easy to adjust the quantity of immobilized heparin.

The immobilizing of heparin by irradiation by light facilitates molding and production.

The protective layer composed of photo-reactive water-soluble macromolecules imparts the hydrophilic properties to a device face when in contact with blood. Therefore, only a small quantity of heparin can be used to develop anti-thrombogenic properties.

Adjustment of the percentage of the photo-reactive group in water-soluble photo-crosslinking macromolecules can control the speed of heparin discharge.

Also, adjustment of the quantity of water-soluble photo-crosslinking macromolecules can control the speed of heparin discharge.

Also, blend of cationic macromolecules into water-soluble photo-crosslinking macromolecules can control the speed of heparin discharge.

The method for immobilizing an anti-thrombogenic substance according to the present invention can be applied to a medical device to be put in contact with blood or to be inserted into a human body for use, such as a catheter, a blood bag, an artificial heart, or an artificial blood vessel. This invention can also provide a medical device having outstanding performance. Specifically, even when the medical device contacts blood or is inserted into a human body, the effective immobilization of the anti-thrombogenic substance in the medical device prevents blood from clotting around the medical device, thereby ensuring the function of the medical device.

This invention has been described above with reference to preferred embodiments as shown in the drawings. Modifications and alterations may become apparent to the one skilled in the art upon reading and understanding the specification. Despite the use of the embodiments for illustration purposes, it is intended to include all such modifications and alterations within the scope and the spirit of the appended claims.

What is claimed is:

1. A method for immobilizing an anti-thrombogenic substance comprising the steps of:
    coating a surface of a base with a bonding layer comprising a photo-reactive azide derivative macromolecular material which provides covalent bonding when exposed to light;
    applying an aqueous solution onto the bonding layer coated base to coat the bonding layer with a macromolecular layer, the aqueous solution including a water-soluble photo-crosslinking macromolecular material and the anti-thrombogenic substance; and
    irradiating the base with both the bonding layer and the macromolecular layer formed thereon with light to fix chemically the macromolecular layer on the base via the bonding layer, the water-soluble photo-crosslinking macromolecular material becoming insoluble and maintaining a gel-condition thereof after being crosslinked by said irradiation;
    wherein the anti-thrombogenic substance is retained in the macromolecular layer.

2. A method according to claim 1, further comprising coating the macromolecular layer with a hydrophilic protective layer of a water-soluble photo-crosslinking macromolecular material, wherein by irradiating the base with the bonding layer, the macromolecular layer and the hydrophilic protective layer formed thereon with light, the macromolecular layer and the hydrophilic protective layer are chemically fixed onto the base via the bonding layer, and the anti-thrombogenic substance is immobilized in the macromolecular layer.

3. A method according to claim 2, wherein the hydrophilic protective layer comprises a mixture of the water-soluble photo-crosslinking macromolecular material and a cationic macromolecular material.

4. A method according to claim 1, wherein the water-soluble photo-crosslinking macromolecular material is a water-soluble macromolecular material including one of a photo-reactive group showing photo-dimeric reaction and a water-soluble macromolecular material having a photo-reactive azide group.

5. A method according to claim 2, wherein the water-soluble photo-crosslinking macromolecular material is a water-soluble macromolecular material including one of a photo-reactive group showing photo-dimeric reaction and a water-soluble macromolecular material having a photo-reactive azide group.

6. A method according to claim 3, wherein the water-soluble photo-crosslinking macromolecular material is a water-soluble macromolecular material including one of a photo-reactive group showing photo-dimeric reaction and a water-soluble macromolecular material having a photo-reactive azide group.

7. A method according to claim 1 further comprising the step of choosing a material selected from the group consisting of poly-m-azidostyrene, copolymers of m-azidostyrene with styrene, and copolymers of m-azidostyrene with methyl methacrylate, as the azide derivative macromolecular material.

8. A device incorporating an immobilized anti-thrombogenic substance comprising:
    a base coated with a bonding layer comprising a photo-reactive azide derivative macromolecular material soluble in an organic solvent chosen from the group of azide derivative macromolecules consisting of poly-m-azidostyrene, copolymers of poly-m-azidostyrene with styrene, and copolymers of poly-m-azidostyrene with methyl methacrylate which provides covalent bonding when exposed to light; and an anti-thrombogenic layer formed by:
    applying an aqueous solution onto the bonding layer coated base to coat the bonding layer with a macromolecular layer, the aqueous solution including a water-soluble photo-crosslinking macromolecular material and the anti-thrombogenic substance;
    irradiating the base with the bonding layer and the macromolecular layer formed thereon with light to fix chemically the macromolecular layer on the base via the bonding layer, the water-soluble photo-crosslinking macromolecular material becoming insoluble and maintaining a gel-condition thereof after being crosslinked by said irradiation.

9. A device according to claim 8, further comprising a coating over the macromolecular layer forming a hydrophilic protective layer of a water-soluble photo-crosslinking macromolecular material cured by the irradiation.

10. A device according to claim 9, wherein the hydrophilic protective layer comprises a mixture of the water-soluble photo-crosslinking macromolecular material and a cationic macromolecular material.

11. A device according to claim 8, wherein the water-soluble photo-crosslinking macromolecular material is a water-soluble macromolecular material including one of a photo-reactive group showing photo-dimeric reaction and a water-soluble macromolecular material having a photo-reactive azide group.

12. A device according to claim 9, wherein the water-soluble photo-crosslinking macromolecular material is a water-soluble macromolecular material including one of a photo-reactive group showing photo-dimeric reaction and a water-soluble macromolecular material having a photo-reactive azide group.

13. A device according to claim 10, wherein the water-soluble photo-crosslinking macromolecular material is a water-soluble macromolecular material including one of a photo-reactive group showing photo-dimeric reaction and a water-soluble macromolecular material having a photo-reactive azide group.

14. A method for immobilizing an anti-thrombogenic substance comprising the steps of:
    dissolving a photo-reactive azide derivative macromolecular material, which provides covalent bonding when exposed to light, in an organic solvent to form a bonding solution;
    coating a surface of a base with the bonding solution to form a bonding layer;
    applying an aqueous solution onto the bonding layer coated base to coat the bonding layer with a macromolecular layer, the aqueous solution including a water-soluble photo-crosslinking macromolecular material and the anti-thrombogenic substance, with the water-soluble photo-crosslinking macromolecular material being a material selected from the group consisting of a water-soluble macromolecular material including a photo-reactive group showing a photo-dimeric reaction and a water-soluble macromolecular material having photo-reactive azide group; and irradiating the base with both the bonding layer and the macromolecular layer formed thereon with light to fix chemically the macromolecular layer on the base via the bonding layer, the water-soluble photo-crosslinking macromolecular material becoming insoluble and maintaining a gel-condition therefor after being crosslinked by said irradiation; wherein the anti-thrombogenic substance is retained in the macromolecular layer after said irradiation.

15. A method according to claim 14 further comprising the step of choosing a material selected from the group consisting of poly-m-azidostyrene, copolymers of m-azidostyrene with styrene, and copolymers of m-azidostyrene with methyl methacrylate, as the azide derivative macromolecular material.

16. A method according to claim 15 further comprising the step of choosing a material selected from the group consisting a copolymer of a photo-dimeric monomer with a water-soluble monomer and a monomer having a photo-reactive azide group with a water-soluble monomer as the water-soluble photo-crosslinking macromolecular material.

17. A method according to claim 16 further comprising the step of choosing a material selected from a group consisting of a cinnamic acid derivative, a chalcone derivative, a cumarin derivative, and a thymine derivative, as the photo-dimeric monomer.

18. A method according to claim 16 further comprising the step of choosing a material selected from the group consisting of acrylamide or dimethylacrylamide, as the water soluble monomer.

19. A method according to claim 15 further comprising the steps of coating the macromolecular layer, containing the anti-thrombogenic substance, with a hydrophilic protective layer of a water-soluble photo-crosslinking macromolecular material.

* * * * *